United States Patent [19]

Murchie

[11] Patent Number: 5,046,512

[45] Date of Patent: Sep. 10, 1991

[54] METHOD AND APPARATUS FOR TREATMENT OF SNORING

[76] Inventor: John A. Murchie, 202 - 1050, Jarvis Street, Vancouver, British Columbia, Canada, V6E 2C1

[21] Appl. No.: 400,353

[22] Filed: Aug. 30, 1989

[30] Foreign Application Priority Data

Mar. 10, 1989 [CA] Canada .................................. 593417

[51] Int. Cl.[5] .............................................. A61F 5/56
[52] U.S. Cl. ..................................... 128/848; 128/859
[58] Field of Search ......................... 128/848, 859–863

[56] References Cited

U.S. PATENT DOCUMENTS

| | | | |
|---|---|---|---|
| 774,446 | 11/1904 | Moulton | 128/848 |
| 1,635,272 | 7/1927 | Hartl | 128/857 |
| 1,674,336 | 6/1928 | King | 128/848 |
| 2,178,128 | 10/1939 | Waite | 128/848 |
| 2,589,504 | 3/1952 | Miller | 128/857 |
| 2,867,212 | 1/1959 | Nunn, Jr. | 128/857 X |
| 3,139,088 | 6/1964 | Galleher, Jr. | 128/857 X |
| 4,261,354 | 4/1981 | Nelson | 128/848 X |
| 4,270,531 | 6/1981 | Blachly | 128/861 X |
| 4,304,227 | 12/1981 | Samelson | 128/857 X |
| 4,640,273 | 2/1987 | Greene et al. | 128/861 |

FOREIGN PATENT DOCUMENTS 751281 6/1956 United Kingdom ................ 128/848

*Primary Examiner*—Robert A. Hafer
*Assistant Examiner*—Kevin G. Rooney
*Attorney, Agent, or Firm*—Barrigar & Oyen

[57] ABSTRACT

The present invention provides an improved method and apparatus for treatment of snoring and apnea. The method provides the steps of regulating the flow of air through the mouth of the user to an extent comparable to the volume of air which flows through the user's nasal passages. The apparatus provides a device having a body portion sufficiently wide to separate the user's teeth and provided with an air passsage comparable in area to the area of the user's nasal passages. In a preferred form of the invention the user is able to seal the air passage with his tongue to completely suppress the flow of air through the mouth and to control the turbulence of the air meeting the nasal inspiration.

4 Claims, 2 Drawing Sheets

METHOD AND APPARATUS FOR TREATMENT OF SNORING

BACKGROUND OF THE INVENTION

The invention relates to the treatment of snoring in humans and more particularly to a method and apparatus for the treatment of snoring and apnea.

DESCRIPTION OF THE PRIOR ART

Snoring, the generation of noise during sleep due to the vibration of the fleshy portions of the pharynx including the uvula, affects a large portion of the population. In its more serious manifestations, snoring can seriously disrupt the sufferer's sleep and may be related to apnea, the periodic cessation of breathing during sleep.

Despite considerable research devoted to the problem of snoring over many years, no progress has been made to a successful treatment for the problem. Various theories have been espoused resulting in a number of methods and apparatus for the treatment of snoring. For example, West German patent No. 65194, issued Nov. 1, 1892 to Otto Francke in Cottbus discloses a device for insertion into the snorer's mouth which has a rubber tube flattened on one end. The flattened end was to be rested on the tip of the tongue as this would keep the tongue moving and the mouth salivating. Apparently it was thought that by keeping the mouth closed and the throat moist, snoring would be reduced. Similarly, in U.S. Pat. No. 746,869 issued Dec. 15, 1903 to Moulton, a mouthpiece having a one-way valve was provided which prevented the ingress of air through the mouth and regulated the egress of air through the mouth. Again it was thought that the flow of air through the mouth caused the drying of the throat which in turn caused snoring and therefore it was thought desirable to cut off all breathing through the mouth.

More recent theories have postulated that snoring might be treated by opening the air passage at the back of the throat by pulling the tongue forward. For example U.S. Pat. No. 4,304,227 issued Dec. 8, 1981 to Samelson and U.S. Pat. No. 4,676,240 issued June 30, 1987 to Gardy disclose devices positioned in the mouth for holding the tongue forward during sleep. U.S. Pat. No. 3,132,647 issued May 12, 1964 to Corniello discloses a device which achieves this result using a metal pad to depress the rear portion of the tongue.

British patent No. 1,248,474 issued Oct. 6, 1971 discloses a device for preventing snoring which keeps the lips apart and allows a restricted amount of breathing through the mouth. This device however does not separate the wearer's teeth and the size of the air passage is such as to be extremely restrictive of air flow through the mouth.

SUMMARY OF THE INVENTION

The present invention provides an improved method and apparatus for treatment of snoring and apnea. The method provides the steps of regulating the flow of air through the mouth of the user to an extent comparable to the volume of air which flows through the user's nasal passages. The apparatus provides a device having a body portion sufficiently wide to separate the user's teeth and provided with an air passage comparable in area to the area of the user's nasal passages. In a preferred form of the invention the user is able to seal the air passage with his tongue to completely suppress the flow of air through the mouth and to control the turbulence of the air meeting the nasal inspiration.

BRIEF DESCRIPTION OF THE DRAWINGS

In drawings which illustrate an embodiment of the invention.

DETAILED DESCRIPTION OF A PREFERRED EMBODIMENT

Figure 1:
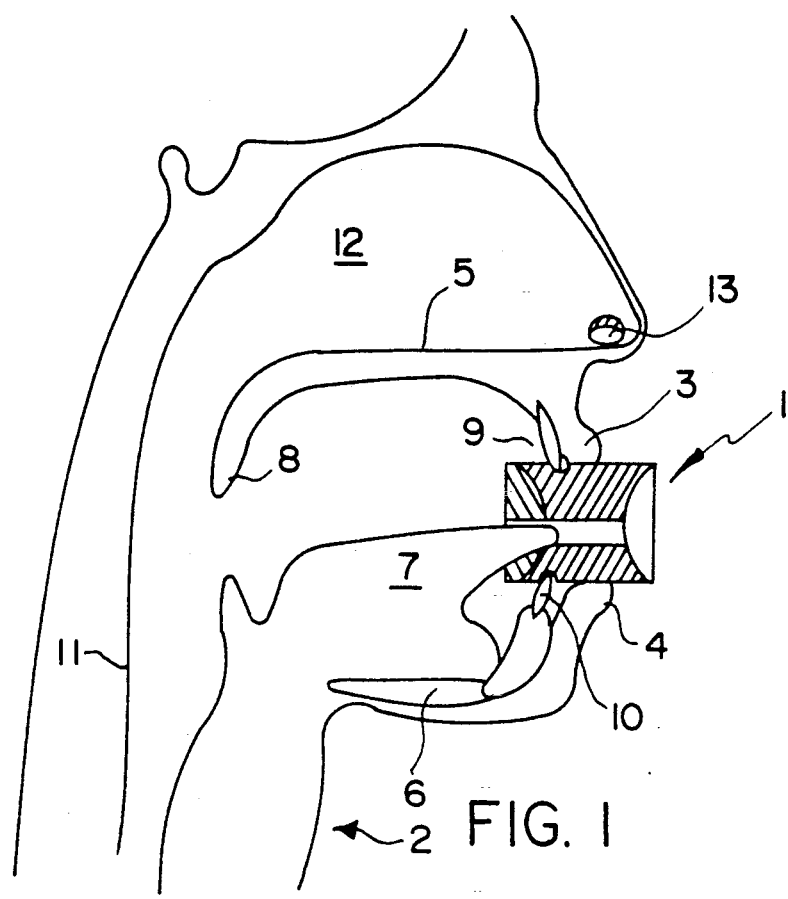
FIG. 1 is a cross-sectional view showing the device of the invention in use in a patient's mouth.
Figure 2:
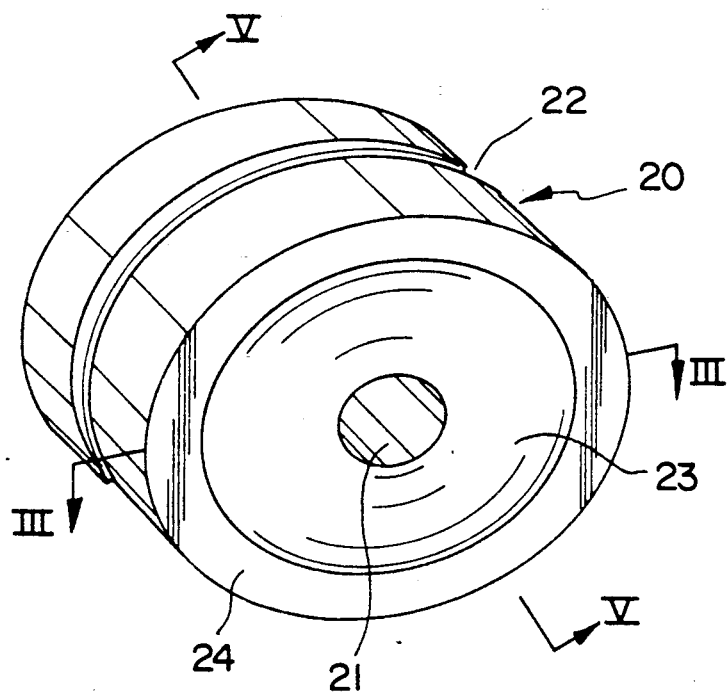
FIG. 2 is a perspective view of the device of the invention.
Figure 3:
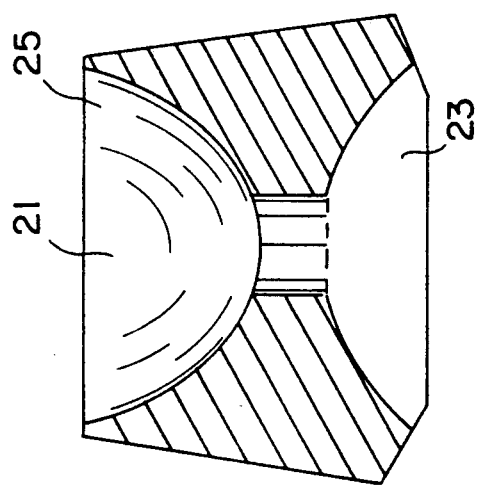
FIG. 3 is a cross-sectional view taken along lines III—III of FIG. 2.
Figure 5:
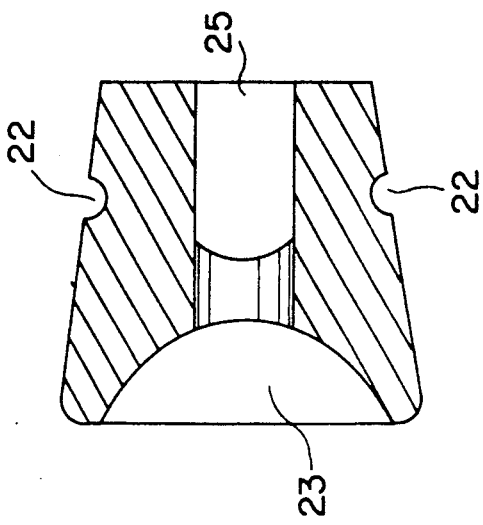
FIG. 5 is a cross-sectional view taken along lines V—V of FIG. 2.
Figure 4:
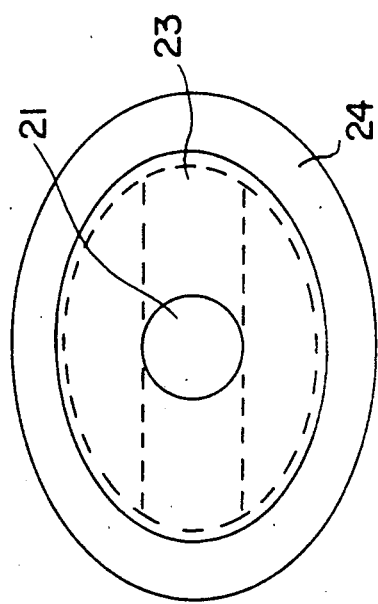
FIG. 4 is front view of the device shown in FIG. 2.

Referring to FIG. 1, the device of the invention, shown as 1, is located in the mouth of a user 2. The mouth has upper lip 3, lower lip 4, upper jaw 5, lower jaw 6, tongue 7, uvula 8, upper teeth 9 and lower teeth 10. The pharynx is designated 11, the nasal cavity as 12 and nostril 13. During normal breathing air is drawn through nostril 13, passes through nasal passage 12 and past pharynx 11 to proceed to the lungs. Normally air flows smoothly past the uvula and pharynx which remain relatively firm. However, snoring is caused when air flowing through the mouth creates turbulence and causes the soft flesh of uvula 8 and pharynx 11 to vibrate.

The device of the present invention is shown in more detail in FIGS. 2 through 5. It consists of a tapered body portion 20 constructed of a moulded plastic or elastomeric material. A circular air passage 21 (referred to herein as a "respiratory orifice") is formed completely through the device. A groove 22 is formed in the outer surface of the device to receive the user's teeth.

A recess 23 is formed in the front surface of the device, forming a rim 24. This construction saves material and lightens the device but is not essential to the invention.

A corresponding recess 25 in the rear surface of the device allows the user to insert his or her tongue to control the flow of air through the device. So long as the user is able to breathe only through his or her nostrils, the user will completely cut off the flow of air through the mouth, avoiding the usual snoring problem. However, if the user is unable to breathe completely through his or her nose due to congestion or the like, the user is able to withdraw the tongue, or it may be withdrawn involuntarily during sleep.

As shown in FIG. 1, when the user's teeth grip the device in groove 22, the user's lips naturally seal around the oval exterior shape of the device. The dimensions of the device vary according to the size of the mouth of the individual, but for the typical adult the device is 1.25 to 1.5 inches long, about 2 inches at maximum front width and 1.5 inches at maximum front height. The separation of the teeth for an adult size device will be about 1.25 inches, while for a child the separation will be about 0.5 inches. This is not taking into account the orthodontical depth of teeth groove 22 which may be up to about 3/16 inches. The slight taper from front to rear facilitates the sealing of the user's lips around the device. The tongue recess allows the user's tongue to extend about 0.75 inches into the device passing beyond the tooth line.

The diameter of air passage 21 has been found to be critical if air is to be taken in through the mouth. It has bee found that the cross-sectional area of the air passage 21 should approximate the corresponding area of the user's nostrils. Typically this means a diameter of approximately ⅜ inches. By limiting the size of the aperture in this way, the volume of air taken in through the mouth approximates the volume normally taken in through the nostrils, also reducing organic dust intake which cause a reaction in the pharynx and may result in involuntary closure of the pharynx.

Any suitable mouldable plastic may be used for the device. A suitable material would be a heat-sensitive synthetic such as ethylene vinyl acetate used for hockey mouth guards which softens sufficiently in hot water to mould the material to the individual's mouth. An orthodontic tooth impression is made by boiling the material repeatedly until a 3/16 inches is made for the teeth. This impression locks the device in place during sleep.

The device thus operates in two modes. When the user's tongue is blocking the air passage, the device effectively seals the mouth passage due to the tapered shape and position of the teeth groove. When air is allowed through the air passage, snoring is prevented by the control of air flow through the air passage and also the thickness of the device between the user's jaws causes the air passage at the rear of the mouth to be opened.

While one beneficial effect of the use of the device has been found to be the reduction of snoring, use of the device has also been found to alleviate apnea, or the cessation of breathing, which may occur during REM sleep. By controlling the flow of air into the mouth, the device apparently provides the patient with a more regular breathing cycle.

CASE STUDY

X was a chronic snorer who reported nocturnal apnea, recurrent nocturnal awakening, unrefreshing sleep and excessive daytime hypersomnolence. X's sleep was monitored in a clinical situation. The invention was put into X's mouth after three hours of sleep. Prior to using the invention, X demonstrated severe snoring and a maximum 72 decibels with associated obstructive hypopnea. After the invention was placed in X's mouth, no further snoring was observed and X awoke in the morning refreshed. The obstructive sleep apnea/hypopnea with associated arterial oxygen desaturation which had been observed was relieved by the use of the invention.

As will be apparent to those skilled in the art various modifications of the structure described above without departing from the spirit of the invention, the scope of which is to be construed in light of the following claims.

The embodiments of the invention in which an exclusive property or privilege is claimed are defined as follows:

1. A method of treating snoring in a human subject having two nostrils, a mouth and tongue, comprising:
    a) measuring the combined cross-sectional area of said nostrils in a direction generally perpendicular to the flow of air through said nostrils;
    b) providing a device for lodging between the subject's lips thereby forming an airtight seal, said device comprising:
        i) a body portion sized to sealingly fit in said subject's mouth, and having a front and a rear surface;
        ii) an air passage formed in said body portion having a cross-sectional area measured in a direction generally perpendicular to the direction of flow of air through said air passage of between 30 percent greater and 30 percent less than the combined cross-sectional area of said nostrils; and
        iii) an aperture formed in said rear surface of said body portion communicating with said air passage and sized to permit said subject to releasably seal said air passage with said tongue; and
    c) placing said device in said subject's mouth during sleep, and permitting said subject to block or unblock said air passage with said tongue according to the subject's need for air through said passage during sleep.

2. The method of claim 1 wherein the cross-sectional area of said air passage is between twenty percent greater and twenty percent less than the combined cross-sectional area of said nostrils.

3. The method of claim 1 wherein the cross-sectional area of said air passage is between ten percent greater and ten percent less than the combined cross-sectional area of said nostrils.

4. The method of claim 1 wherein the cross-sectional area of said air passage is approximately equal to or slightly less than the combined cross-sectional area of said nostrils.

* * * * *